United States Patent [19] [11] Patent Number: 4,581,371
Baldacci [45] Date of Patent: Apr. 8, 1986

[54] PHARMACEUTICAL COMPOSITION HAVING IMMUNOMODULATING ACTIVITY

[75] Inventor: Massimo Baldacci, Pisa, Italy

[73] Assignee: Laboratori Baldacci S.p.A., Pisa, Italy

[21] Appl. No.: 476,499

[22] Filed: Mar. 18, 1983

[30] Foreign Application Priority Data

Mar. 18, 1982 [IT] Italy .............................. 20251 A/82

[51] Int. Cl.$^4$ ............................................. A61K 31/40
[52] U.S. Cl. .................................................. 514/423
[58] Field of Search ........................ 424/274; 514/423

[56] References Cited

FOREIGN PATENT DOCUMENTS 2224154 12/1974 France ............................... 424/274

OTHER PUBLICATIONS

Van der Wef, Paul, J. Biol. Chem., vol. 250, No. 17 (1975), pp. 6686-6692.
Merister, A., TIBS, vol. 6, No. 9, (1981) pp. 231-234.
Fabrio, N., Clin Exp. Immunol., vol. 15, (1973) pp. 601-611.
Isidori, A. et al., Current Medical Research And Opinion, vol. 7, No. 7 (1981) pp. 425-481.
Fabris, N. et al., Clin. exp. Immunol., vol. 28, (1977) pp. 315-325.
Chem. Abst. 95:138392x, Shiseido Co., Ltd. (6/18/81).
Chem. Abst. 83:202005e, Societa Italo (10/31/84).
Chem. Abst. 68:103689g, Massimo, (1968).
Chem. Abst. 80:149097w, Pilet et al. (1974).
Chem. Abst. 95: 181678g, Isideri et al. (1981).

*Primary Examiner*—Stanley J. Friedman
*Assistant Examiner*—Freda Abramson
*Attorney, Agent, or Firm*—Martin Smolowitz

[57] ABSTRACT

The administration by oral route of a composition comprising arginine pyrrolidone carboxylate and lysine pyrrolidone carboxylate at a dose of 150 to 200 mg/kg of body weight has immunomodulating activity capable of restoring depressed immunodefenses.

2 Claims, No Drawings

PHARMACEUTICAL COMPOSITION HAVING IMMUNOMODULATING ACTIVITY

The present invention relates to a pharmaceutical composition having immunomodulating activity useful both in elderly people having depressed immunodefenses and in children especially those often taken ill by tonsillitis and consequently in all pathologies with altered immunodefenses.

The importance is evident of being able to stimulate, by oral administration of modest doses of amino acids, the defense mechanism by which biological immunity is maintained by the immunosystem of an organism.

It has now been found that lysine and arginine, when salified with pyrollidonecarboxylic acid and administered to elderly mice, orally at a dose of 2 g/kg, either alone or associated cause an increase of immunological efficiency which can be detected from a significant increase of the response to phytohemagglutinin measuring the efficiency of the T mature lymphocytes (T2), and from a significant increase of the circulating thymic factor (F.T.S.) by which the level of endocrine activity of the thymus is measured.

On the basis of these experimental premises the present invention was made, according to which the administration to the human being of the two amino acids orally and at a dose of 120 mg/kg, induces an immunomodulating action, capable of restoring to normal level states of immunological deficiency. It is known that the pyrrolidonecarboxylic acid (P.C.A.) cyclic lactam of glutamic acid, is a compound which only recently found a place in the cell metabolic picture (Van der Verf et al, 1975).

The P.C.A. function in amino acid metabolism is strictly related to the synthesis of glutathione and to the role played by this tripeptide in the γ-glutamyl cycle.

P.C.A. for this relationship becomes potentially active for those processes in which the protective and coenzymatic functions of glutathione are involved (Meister, 1981).

The function of amino acid carrier by the enzymatic system forming the γ-glutamyl cycle is supported by a number of experimental evidences.

The γ-glutamyl residue of glutathione is transferred to the acceptor amino acid by action of γ-glutamyl transpeptidase, an enzyme which is located in the sites involved in the carrying processes such as the brushlike edge of the kidney and intestinal cells or the epithelium of the ciliary body (Allutt et al, 1961).

The γ-glutamyl amino acid strictly associated with the membrane is transferred to the inside of the cell thus becoming the substrate for the γ-glutamyl cyclotransferase.

Such an enzyme causes the transported amino acid to be released in the cytoplasm and P.C.A. to be formed (Van der Vers et al, 1975). The thus formed P.C.A. is recycled for the synthesis of glutathione, through a previous conversion into glutamate by means of 5-oxoprolinase, according to two subsequent reactions which are catalyzed by γ-glutamylcysteine synthetase and by glutathione synthetase.

The P.C.A. is quickly absorbed and distributed in vivo in the several organs and tissues. This essential condition for the occurrence of whatever pharmacological action of P.C.A. has been assessed by using rats to which were administered $C^{14}$ P.C.A. per os and by i.p. route. The results obtained by using kidney, liver and brain show an accumulation of P.C.A. of between 20 and 250 n.moles per g of tisssue as examined in view of the radioactivity incorporated hereinto. Upon having assessed the possibility of increasing the cellular availability of P.C.A., the possible consequent activation of the amino acid transport was investigated.

Both $C^{14}$ lysine and $C^{14}$-arginine were used as markers to follow in vivo the captation process.

The results obtained from the kinetic point of view of the level of distribution in the blood, in the kidney, in the brain and in the liver of rats treated with the marked amino acids, show, in the presence of P.C.A., an increase of the incorporated radioactivity.

A like activation of the amino acid transport which is perfectly integrated with the assumed function of P.C.A. in the cycle of p-glutathione is derived from the higher efficiency of the arginine transport in the presence of P.C.A. which can be detected in hepatic cells in culture.

This activation of the transport of the arginine and lysine amino acids owing to P.C.A. may explain how these amino acids, either alone or better still if associated, are capable of stimulating the secretion of growth hormone (GH) and of insulin. 1200 mg of arginine PCA and 1200 mg of lysine (HCL) administered orally in only one dose improves the secretion of insulin and of GH. 2400 mg of arginine administered orally has no effect (Isidori, 1981).

The combination of the two amino acids salified with P.C.A., when orally administered, is capable of stimulating the secretion of GH and insulin at doses of 120 mg/kg of body weight, whereas it is known that, in order to evaluate the hypophysary reserve of GH, 500 mg/kg of body weight by i.v. route are necessary.

By observing that these hormones (GH, insulin) are not only essential for a correct development of the immunological system (Fabris et al, 1973) and for maintaining immunological efficiency (Fabris et al, 1973), but also play a role in the aging of said system (Fabris et al, 1977), the present invention was made.

It is thus evident that the immunomodulating activity of arginine and lysine pyrrolidonecarboxylate was and is wholly unexpected and surprising.

For the administration of the subject active composition, in view of the type of therapeutical effect sought, the oral route is foreseen with dosages of the order of 1 g of each active ingredient, without occurrence of gastro-intestinal intolerance or changes of the hepatic or renal functionality.

The administration takes place at the end of the chemotherapy by leaving enough time (15 to 21 days) before the next cycle of treatment with antiblastic chemotherapeutical drugs is started again.

With respect to the composition of the present invention pharmacological and clinical tests were carried out, which are hereinafter synthetically reported.

(A) Action on the immunodeficiency of elderly mice.

Groups of 8 male mice Balb/C inbred, 24 months old, were treated for 15 consecutive days with a composition (hereinafter referred to as NIA) having the following formulation.

L-2-pyrrolidone-5-carboxylate of L-lysine (LPCA): 1 g

L-2-pyrrolidone-5-carboxylate of L-arginine (APCA): 1 g potassium iodide: 0.001 g sodium benzoate: 0.0354 g fructose: 7.500 g ascorbic acid: 0.0075 g
sodium metabisulfite: 0.0075 g
lemon flavor: 0.060 g
deionized water: to 15 ml.

The treatment was also carried out with the single amino acids at doses of 1 and 10 DTS. At the end of the treatment the following immunological parameters were evaluated in the sacrificed animals:

(1) Response of the spleen cells to the phytohemagglutinin (PHA) measuring the efficiency of the mature T lymphocytes ($T_2$).

(2) Response of the spleen cells to the concanavallin A (Con-A) measuring the efficiency of $T_1$ cells (less mature step) besides that of the $T_2$ population (3) Response of the spleen cells to lipopolysaccharide (LPS), measuring the efficiency of the B population.

(4) The ratio PHA:Con-A, which is an index of the maturity degree of the peripheral lymphocytes (in old people a more remarkable decline of $T_2$ owing to the non-maturation from $T_1$ to $T_2$ is noticed).

(5) The level of the circulating thymic factor (FTS), measuring the level of endocrine activity of the thymus and which is prematurely lowered with age.

Such an age-dependent problem is not related to an intrinsic alteration of the organ and may be corrected through a suitable treatment with thyroxine.

From the above investigations it resulted that the NIA composition, administered at the dose of 1 DTS to elderly mice for 15 consecutive days, induced an increase of the efficiency of the immunological system, which can be put into evidence at the level of:

(1) response to PHA
(2) level of FTS
(3) PHA:Con-A ratio.

At a dose of 10 DTS the increase is higher and a significant increase of the response to Con-A is also observed.

The LPCA, when administered at a dose of 1 or 10 DTS, shows an action on the response to PHA and on the FTS level; the effect on the response to Con-A does not attain significant levels.

The APCA is likely active on the response to PHA and to Con-A, as well as on the FTS level.

(B) Clinical Tests

There were evaluated 50 patients divided into three groups:

GROUP A

It comprised 20 patients, between 37 and 84 years old (average: 67.4±12.2) affected by chronic hepatitis or cirrhosis of the liver, and treated with NIA with a posology of two vials per os every 12 hours for a period of 30 days.

GROUP B

It comprised 20 patients, between 46 and 97 years old (average 65±21.3) affected by neoplastic diseases of various types and treated with NIA with a posology of two vials per os every 12 hours for a variable period of between 25 and 30 days (average: 28.9±2.4)

GROUP C

It comprised 10 patients, between 46 and 83 years old (average: 62.7±11.7), affected by neoplastic diseases of various types, and treated with BCG Pasteur applied by multiple cutaneous scarifications at a posology of 75 mg two times each day for three consecutive days. In all patients, at the beginning and at the end of the treatment, there were evaluated:

(1) rosette E (rosette erythrocyte)
(2) rosette E"active"
(3) rosette EAC (erythrocyte antibody complement)
(4) immunoglobulins
IGC (immunoglobulin C)
IGA (immunoglobulin A)
IGM (immunoglobulin M)
(5) skin tests
a. PPD (purified protein derivative)
b. Candida
c. Streptokinase/streptodornase
d. Tricophyton Moreover, at the beginning and at the end of the treatment, there were evaluated:
(1) Azotemia
(2) Glycemia
(3) Creatininemia
(4) SGOT
(5) SGPT The results are reported in tables 1, 2 and 3.

The purpose of the experiments was that of assessing whether the drug might modify the cell-mediate and the humoral immunity.

To this end there were treated patients having iatrogenic immunodeficiencies, namely induced by immunosuppressing therapies (chemotherapeutical, antiblastic and/or corticosteroidal drugs).

Those patients were classified as immunodepressed who had hyporeactivity to skin tests, a low number of rosette E, of rosette E "active", of rosette EAC and a low level of serum immunoglobulins. The analysis of the results lead to the conclusion that the administration of NIA in these patients is able to induce a series of events leading to a stimulation of the immune system.

After the administration of the drug there was observed an increase of the reactions of hypersensitivity to the common antigens; likewise the percentage of lymphocytes B and T, as detectable through the rosette tests, did undergo a remarkable increase.

The serum levels of immunoglobulins were also influenced by the administration of the drug.

It is also interesting to note the comparison between the patents subjected to immunotherapy with BCG and the NIA treated patients.

In both groups an increase of the immune response, mainly of the cell-mediate type, was observed after stimulation with BCG, whereas NIA demonstrated also an efficacy in increasing the percentage of serum immunoglobulins.

It is furthermore to be pointed out the absolute absence of side effects after NIA administration, whereas after BCG immunotherapy there were sometimes detected side effects, even if of a transient nature (hyperthermy, adenomegaly).

TABLE 1

| | GROUP A | | | |
|---|---|---|---|---|
| TREATM. | ROSETTE E | ROSETTE E "active" | ROSETTE EAC | IGG |

TABLE 1-continued

| | | | | | GROUP A | | | | | | | | |
|---|---|---|---|---|---|---|---|---|---|---|---|---|---|
| CASE | NAME | AGE | SEX | DAYS | p | d | p | d | p | d | p | d | |
| 1 | P.C. | 60 | M | 30 | 30 | 60 | 15 | 25 | 6 | 12 | 400 | 1000 | |
| 2 | C.L.B. | 83 | M | 30 | 30 | 70 | 15 | 15 | 8 | 10 | 600 | 1000 | |
| 3 | G.B. | 75 | M | 30 | 30 | 70 | 10 | 25 | 13 | 24 | 1000 | 1200 | |
| 4 | A.D.G. | 84 | M | 30 | 40 | 60 | 20 | 25 | 7 | 12 | 400 | 1200 | |
| 5 | C.C. | 65 | M | 30 | 40 | 70 | 15 | 23 | 10 | 13 | 1000 | 1850 | |
| 6 | R.R. | 77 | F | 30 | 30 | 70 | 20 | 25 | 17 | 22 | 600 | 900 | |
| 7 | A.F. | 69 | M | 30 | 30 | 70 | 20 | 25 | 15 | 22 | 700 | 1100 | |
| 8 | L.D.L. | 75 | F | 30 | 30 | 60 | 20 | 30 | 15 | 25 | 700 | 1100 | |
| 9 | F.M. | 79 | F | 30 | 30 | 60 | 20 | 30 | 17 | 25 | 400 | 1000 | |
| 10 | M.C.D.S | 52 | F | 30 | 25 | 60 | 20 | 30 | 15 | 20 | 400 | 1200 | |
| 11 | F.V. | 71 | F | 30 | 30 | 70 | 20 | 25 | 15 | 20 | 850 | 1800 | |
| 12 | C.B. | 77 | F | 30 | 30 | 60 | 20 | 25 | 15 | 20 | 600 | 1100 | |
| 13 | R.P. | 56 | F | 30 | 28 | 66 | 20 | 25 | 15 | 17 | 800 | 1700 | |
| 14 | R.D.R. | 69 | M | 30 | 35 | 70 | 22 | 27 | 20 | 25 | 700 | 1100 | |
| 15 | C.T. | 48 | F | 30 | 30 | 70 | 20 | 25 | 15 | 20 | 800 | 1800 | |
| 16 | R.S. | 37 | M | 30 | 25 | 60 | 15 | 25 | 15 | 22 | 800 | 1200 | |
| 17 | C.C. | 59 | M | 30 | 30 | 70 | 20 | 25 | 15 | 20 | 600 | 1800 | |
| 18 | A.S.M. | 66 | F | 30 | 30 | 70 | 22 | 25 | 15 | 20 | 600 | 1300 | |
| 19 | A.F. | 69 | M | 30 | 30 | 65 | 25 | 30 | 15 | 17 | 880 | 1900 | |
| 20 | E.F. | 77 | F | 30 | 27 | 52 | 20 | 25 | 15 | 20 | 350 | 900 | |
| | | 67,4 ± 12,2 | | 30 | 30,5 ± 3,8 | 65,2 ± 5,5 | 18,9 ± 3,3 | 25,5 ± 3,2 | 13,9 ± 3,4 | 19,3 ± 4,5 | 659 ± 200 | 1307 ± 352 | |

| | IGA | | IGM | | PPD | | CANDIDA | | STREPTOKINASE STREPTODORNASE | | TRICOPHYTON | |
|---|---|---|---|---|---|---|---|---|---|---|---|---|
| CASE | p | d | p | d | p | d | p | d | p | d | p | d |
| 1 | 40 | 300 | 240 | 280 | + | +++ | − | ++ | + | + | − | + |
| 2 | 40 | 80 | 100 | 200 | + | ++ | − | + | + | + | − | − |
| 3 | 40 | 300 | 400 | 380 | + | +++ | − | ++ | − | + | + | ++ |
| 4 | 60 | 250 | 300 | 300 | + | +++ | + | + | − | ++ | + | +++ |
| 5 | 60 | 115 | 250 | 250 | ++ | +++ | + | +++ | − | + | − | − |
| 6 | 100 | 150 | 100 | 120 | + | +++ | + | ++ | + | + | + | ++ |
| 7 | 80 | 100 | 90 | 100 | + | +++ | + | + | − | + | + | ++ |
| 8 | 70 | 120 | 50 | 100 | + | ++ | + | + | + | + | + | ++ |
| 9 | 150 | 200 | 180 | 250 | + | ++ | − | + | + | ++ | + | ++ |
| 10 | 200 | 250 | 100 | 150 | + | ++ | − | + | + | ++ | + | + |
| 11 | 150 | 200 | 120 | 150 | ++ | +++ | − | ++ | + | + | + | + |
| 12 | 150 | 200 | 200 | 300 | + | ++ | + | ++ | − | + | + | + |
| 13 | 150 | 200 | 100 | 150 | + | ++ | + | + | − | + | + | + |
| 14 | 200 | 250 | 120 | 150 | + | +++ | + | ++ | + | + | + | + |
| 15 | 150 | 300 | 100 | 150 | + | ++ | − | + | + | + | + | ++ |
| 16 | 150 | 250 | 100 | 150 | + | +++ | − | + | + | + | + | ++ |
| 17 | 180 | 200 | 120 | 150 | + | ++ | + | + | − | + | + | +++ |
| 18 | 100 | 200 | 250 | 400 | + | +++ | + | + | + | + | + | ++ |
| 19 | 150 | 180 | 100 | 150 | ++ | +++ | + | ++ | − | + | + | ++ |
| 20 | 200 | 250 | 100 | 200 | + | +++ | + | + | + | ++ | − | + |
| | 121 ± 56 | 204 ± 66 | 156 ± 89,4 | 204 ± 88 | | | | | | | | |

TABLE 2

| | | | | | GROUP B | | | | | | |
|---|---|---|---|---|---|---|---|---|---|---|---|
| | | | | TREATM. | ROSETTE E | | ROSETTE E "active" | | ROSETTE EAC | | IGG |
| CASE | NAME | AGE | SEX | DAYS | p | d | p | d | p | d | p | d |
| 1 | R.A. | 50 | M | 30 | 45 | 65 | 10 | 20 | 16 | 23 | 400 | 1300 |
| 2 | F.G. | 69 | F | 30 | 30 | 70 | 15 | 25 | 10 | 25 | 600 | 1500 |
| 3 | O.P. | 56 | M | 30 | 43 | 65 | 11 | 22 | 15 | 25 | 500 | 1300 |
| 4 | F.I. | 72 | M | 30 | 40 | 75 | 10 | 24 | 3 | 20 | 259 | 1200 |
| 5 | A.Z. | 76 | F | 30 | 40 | 70 | 13 | 22 | 14 | 25 | 700 | 1400 |
| 6 | A.L. | 85 | F | 30 | 20 | 65 | 10 | 20 | 7 | 18 | 350 | 700 |
| 7 | E.L. | 73 | F | 30 | 20 | 60 | 15 | 19 | 10 | 22 | 180 | 700 |
| 8 | L.M.P. | 68 | F | 30 | 31 | 60 | 17 | 25 | 12 | 25 | 600 | 1000 |
| 9 | F.B. | 72 | M | 30 | 30 | 70 | 20 | 25 | 15 | 22 | 800 | 1200 |
| 10 | A.A. | 73 | M | 25 | 32 | 60 | 17 | 30 | 10 | 25 | 700 | 1000 |
| 11 | A.F. | 50 | F | 30 | 28 | 60 | 17 | 19 | 12 | 17 | 800 | 1200 |
| 12 | P.M.V. | 83 | M | 30 | 28 | 70 | 20 | 28 | 15 | 22 | 600 | 1100 |
| 13 | C.B. | 97 | F | 30 | 25 | 45 | 15 | 25 | 12 | 17 | 600 | 1000 |
| 14 | M.T.Z. | 68 | F | 26 | 30 | 60 | 20 | 25 | 15 | 22 | 700 | 1200 |
| 15 | A.F. | 65 | F | 30 | 30 | 65 | 18 | 22 | 14 | 18 | 700 | 1150 |
| 16 | M.R. | 56 | F | 24 | 29 | 65 | 25 | 28 | 20 | 25 | 600 | 1200 |
| 17 | G.P. | 46 | F | 22 | 28 | 60 | 20 | 30 | 15 | 25 | 700 | 1200 |
| 18 | M.P. | 77 | M | 30 | 30 | 60 | 20 | 27 | 15 | 20 | 700 | 1000 |
| 19 | F.V. | 61 | M | 30 | 30 | 70 | 20 | 25 | 15 | 20 | 600 | 1100 |
| 20 | M.A.C. | 81 | F | 30 | 30 | 65 | 20 | 25 | 15 | 20 | 700 | 1000 |
| | | 65 ± | | 28,9 ± | 31,5 ± | 64 ± | 16,6 ± | 24,3 ± | 13 ± | 21,8 ± | 589 ± | 1122 ± |

TABLE 2-continued

GROUP B

| | 21,3 | | 2,4 | | 6,2 | 6,4 | 4,2 | 3,3 | 3,6 | 2,9 | 170 | 198 |
|---|---|---|---|---|---|---|---|---|---|---|---|---|

| | IGA | | IGM | | PPD | | CANDIDA | | STREPTOKINASE STREPTODORNASE | | TRICOPHYTON | |
|---|---|---|---|---|---|---|---|---|---|---|---|---|
| CASE | p | d | p | d | p | d | p | d | p | d | p | d |
| 1 | 40 | 65 | 50 | 175 | + | +++ | − | − | + | ++ | − | + |
| 2 | 35 | 100 | 40 | 100 | + | +++ | − | + | + | ++ | + | + |
| 3 | 45 | 70 | 70 | 175 | ++ | +++ | − | + | − | + | − | + |
| 4 | 1230 | 1400 | 18 | 270 | + | +++ | + | ++ | − | + | + | + |
| 5 | 30 | 90 | 35 | 100 | + | ++ | − | ++ | − | + | + | + |
| 6 | 60 | 200 | 40 | 90 | ++ | +++ | − | + | − | + | + | + |
| 7 | 1370 | 1300 | 30 | 90 | − | +++ | − | + | + | + | + | + |
| 8 | 50 | 100 | 40 | 100 | + | ++ | + | + | − | + | + | + |
| 9 | 100 | 150 | 120 | 120 | + | ++ | + | +++ | + | ++ | + | + |
| 10 | 50 | 90 | 40 | 100 | + | ++ | − | + | + | + | + | + |
| 11 | 60 | 100 | 90 | 100 | + | ++ | − | + | + | ++ | + | + |
| 12 | 100 | 150 | 90 | 100 | + | ++ | + | +++ | + | + | + | ++ |
| 13 | 60 | 80 | 80 | 100 | + | +++ | + | ++ | + | + | + | + |
| 14 | 50 | 100 | 60 | 90 | + | ++ | − | + | + | ++ | + | + |
| 15 | 120 | 140 | 100 | 120 | + | +++ | − | + | − | + | + | ++ |
| 16 | 70 | 100 | 60 | 70 | + | '++ | + | ++ | − | + | + | + |
| 17 | 60 | 100 | 45 | 90 | + | ++ | + | ++ | + | +++ | + | + |
| 18 | 100 | 150 | 90 | 120 | ++ | +++ | − | + | − | + | + | ++ |
| 19 | 130 | 150 | 90 | 150 | + | +++ | + | ++ | + | + | + | ++ |
| 20 | 150 | 200 | 100 | 150 | ++ | +++ | + | + | − | + | − | − |
| | 195 ± 379 | 241 ± 381 | 64,4 ± 28,7 | 120,5 ± 45,4 | | | | | | | | |

TABLE 3

GROUP C

| CASE | NAME | AGE | SEX | TREATM. DAYS | ROSETTE E | | ROSETTE E "active" | | ROSETTE EAC | | IGG | |
|---|---|---|---|---|---|---|---|---|---|---|---|---|
| | | | | | p | d | p | d | p | d | p | d |
| 1 | A.D.P. | 63 | M | 3 | 30 | 60 | 20 | 25 | 17 | 20 | 700 | 1000 |
| 2 | G.R. | 82 | M | 3 | 30 | 60 | 20 | 25 | 15 | 20 | 700 | 1000 |
| 3 | P.G. | 55 | F | 3 | 30 | 60 | 20 | 25 | 15 | 20 | 800 | 1000 |
| 4 | P.P. | 46 | F | 3 | 30 | 60 | 19 | 25 | 15 | 20 | 800 | 1000 |
| 5 | L.S. | 58 | M | 3 | 30 | 65 | 22 | 30 | 15 | 20 | 300 | 600 |
| 6 | C.M.M. | 83 | M | 3 | 25 | 60 | 20 | 30 | 20 | 25 | 350 | 500 |
| 7 | D.N. | 67 | F | 3 | 30 | 60 | 27 | 30 | 16 | 25 | 600 | 800 |
| 8 | L.D.S. | 58 | F | 3 | 30 | 60 | 20 | 30 | 15 | 20 | 450 | 800 |
| 9 | A.D.C. | 55 | F | 3 | 32 | 60 | 20 | 30 | 15 | 20 | 350 | 800 |
| 10 | M.C. | 60 | F | 3 | 30 | 60 | 20 | 40 | 15 | 22 | 450 | 800 |
| | | | | | 29,7 ± 1,7 | 60,5 ± 1,6 | 20,8 ± 2,3 | 29 ± 4,6 | 15,8 ± 1,6 | 21,2 ± 2,1 | 550 ± 19,9 | 830 ± 17,6 |
| | | | | | $p < 0.01$ | | $p < 0.01$ | | $p < 0.01$ | | $p < 0.01$ | |

| | IGA | | IGM | | PPD | | CANDIDA | | STREPTOKINASE STREPTODORNASE | | TRICOPHYTON | |
|---|---|---|---|---|---|---|---|---|---|---|---|---|
| CASE | p | d | p | d | p | d | p | d | p | d | p | d |
| 1 | 90 | 100 | 100 | 100 | ++ | +++ | + | + | + | + | − | + |
| 2 | 150 | 200 | 100 | 110 | + | ++ | − | + | − | + | − | + |
| 3 | 100 | 110 | 100 | 110 | ++ | +++ | − | + | + | + | − | + |
| 4 | 110 | 150 | 95 | 110 | + | ++ | + | ++ | − | + | + | + |
| 5 | 90 | 120 | 90 | 100 | + | ++ | − | + | − | + | + | + |
| 6 | 100 | 150 | 100 | 200 | + | ++ | − | − | + | + | − | + |
| 7 | 150 | 160 | 90 | 100 | + | ++ | − | − | − | − | − | − |
| 8 | 100 | 150 | 90 | 120 | ++ | ++ | − | − | − | + | + | + |
| 9 | 90 | 100 | 90 | 110 | + | + | − | − | + | ++ | − | − |
| 10 | 100 | 150 | 90 | 100 | + | ++ | + | + | − | − | − | − |
| | 108 ± 22,9 | 139 ± 31,4 | 94,5 ± 4,9 | 116 ± 3,1 | | | | | | | | |

The previously reported resusts clearly show immunomodulating effect of the pharmaceutical composition according to the invention, the active ingredient of which is arginine pyrrolidonecarboxylate combined with lysine pyrrolidonecarboxylate; thus, in fact, besides the effect of restoring the immunodefense system of the organism, there are also benefits related to the other indications of this combination, especially as regards stimulation of the insulin secretion. It however shall not be construed as an undue limitation of the scope of the invention.

I claim:

1. A method for restoring depressed immunodefenses comprising administering orally to a patient having depressed immunodefenses an immunomodulating composition comprising immunomodulating effective amounts of L-arginine and L-lysine as their salts with L-2-pyrrolidone-5-carboxylic acid.

2. The method according to claim 1, wherein the composition is administered in a daily dosage of 150 to 200 mg per kg of body weight.

* * * * *